US012755836B2

(12) United States Patent
Picot et al.

(10) Patent No.: US 12,755,836 B2
(45) **Date of Patent: *Oct. 6, 2026**

(54) MEDICATION REMINDER DEVICE

(71) Applicants: Bimla Picot, Southampton, NY (US); Bedros Bedrossian, Southampton, NY (US)

(72) Inventors: Bimla Picot, Southampton, NY (US); Bedros Bedrossian, Southampton, NY (US)

( * ) Notice: Subject to any disclaimer, the term of this patent is extended or adjusted under 35 U.S.C. 154(b) by 4 days.

This patent is subject to a terminal disclaimer.

(21) Appl. No.: 18/615,084

(22) Filed: Mar. 25, 2024

(65) Prior Publication Data

US 2024/0233934 A1 Jul. 11, 2024

Related U.S. Application Data

(63) Continuation-in-part of application No. 16/171,547, filed on Oct. 26, 2018, now Pat. No. 11,938,096.

(60) Provisional application No. 62/694,572, filed on Jul. 6, 2018, provisional application No. 62/578,143, filed on Oct. 27, 2017.

(51) Int. Cl.

*G16H 40/63* (2018.01)
*A41B 1/08* (2006.01)
*A41D 1/00* (2018.01)
*A41D 1/06* (2006.01)

(52) U.S. Cl.

CPC ............... *G16H 40/63* (2018.01); *A41B 1/08* (2013.01); *A41D 1/002* (2013.01); *A41D 1/06* (2013.01)

(58) Field of Classification Search

CPC . A41B 1/08; A41D 1/002; A41D 1/06; A41D 13/1236; G16H 20/10

See application file for complete search history.

(56) References Cited

U.S. PATENT DOCUMENTS

| | | | | |
|---|---|---|---|---|
| 5,554,967 | A | 9/1996 | Cook et al. | |
| 7,688,036 | B2 | 3/2010 | Yarger et al. | |
| 2011/0040220 | A1* | 2/2011 | Holgreen | A61H 9/0078 601/148 |
| 2012/0319404 | A1* | 12/2012 | Joseph | H02J 7/32 290/50 |
| 2013/0285479 | A1 | 10/2013 | Kinoshita | |

(Continued)

FOREIGN PATENT DOCUMENTS

| | | | | |
|---|---|---|---|---|
| WO | WO9501622 | | 1/1995 | |
| WO | WO-9501622 | A1 * | 1/1995 | G08B 6/00 |

*Primary Examiner* — Sisay Yacob

(74) *Attorney, Agent, or Firm* — Dority & Manning, P.A.

(57) ABSTRACT

In general, the present disclosure is directed to a reminder device. The reminder device includes an electromechanical transduction device configured to generate electrical energy when agitated by a laundry machine during the course of a washing cycle or a drying cycle, an electrical energy storage device, an electrical coupling between the energy storage device and the electromechanical transduction device, a tactile alert device, an onboard computing device for triggering tactile alerts according to a schedule, a user interface device for acknowledging receipt of the tactile alert, and, in some embodiments, a fixture device for supporting an electrical device housing within a garment and/or a wireless connectivity device for receiving alert schedules and transmitting alert acknowledgements in conjunction with a hub.

18 Claims, 7 Drawing Sheets

(56) References Cited

U.S. PATENT DOCUMENTS

| | | | | |
|---|---|---|---|---|
| 2015/0020288 | A1* | 1/2015 | Picot | A41D 13/129<br>2/69 |
| 2015/0145671 | A1* | 5/2015 | Cohen | G06Q 30/0241<br>340/539.11 |
| 2015/0349556 | A1* | 12/2015 | Mercando | H04W 4/80<br>455/573 |
| 2016/0241119 | A1 | 8/2016 | Keeler | |
| 2016/0342767 | A1 | 11/2016 | Narasimhan et al. | |
| 2017/0085688 | A1 | 3/2017 | Zhou | |
| 2017/0288443 | A1 | 10/2017 | Kursula et al. | |
| 2018/0349561 | A1 | 12/2018 | Lecamus | |

* cited by examiner

MEDICATION REMINDER DEVICE

RELATED APPLICATIONS

The present application claims priority to U.S. Provisional Application Ser. No. 62/578,143, filed on Oct. 27, 2017, U.S. Provisional Application Ser. No. 62/694,572, filed on Jul. 6, 2018, and U.S. application Ser. No. 16/171,547, filed Oct. 26, 2018 which are both incorporated herein in their entirety by reference thereto.

BACKGROUND

The present disclosure is directed to a garment designed for patients to wear throughout the course of long-term care regimens that improves patient comfort and the quality of patient care. After a patient undergoes an initial treatment or surgery, comprehensive follow-up care may continue for weeks, months, or years and can be tiring for both the patient and the attending healthcare professionals. When patients are exasperated, uncomfortable, or uncooperative, the road to recovery can be difficult for all involved.

Patients can be overwhelmed with the number and variety of medications that need to be taken at various intervals. Forgotten or misremembered doses can have severe consequences on a patient's health and wellbeing. While staying in a healthcare facility, a patient may have consistent reminders from the staff, but those in outpatient care cannot always rely upon such close attention. The decreasing cost and increasing capability of mobile technology has enabled innovations which directly assist healthcare professionals with remotely monitoring recovering patients and managing their medication schedules, but the cost and labor required to support such systems are a barrier to scalable adoption by healthcare providers. Furthermore, patients may be frustrated by integrating a new technology into their normal routine.

Patients may also experience discomfort or embarrassment if the particular nature of their injury requires caretaker attention to body parts normally not accessible when wearing normal street clothing. The patients' options may include undressing for the examination or the use of healthcare-oriented clothing which calls attention to their particular injury or disability. Either option presents a potential discouragement to enthusiastic and committed patient cooperation with the prescribed recovery plan.

The present disclosure is a comprehensive rehabilitation garment concept that provides patients with clothing constructed to maintain comfort and dignity while simultaneously addressing the need for patient reminders by incorporating wearable technology designed for easy use and scalable deployment.

SUMMARY

In general, the present disclosure is directed to a reminder device. The reminder device includes an electromechanical transduction device configured to generate electrical energy when agitated by a laundry machine during the course of a washing cycle or a drying cycle, an electrical energy storage device, an electrical coupling between the energy storage device and the electromechanical transduction device, a tactile alert device, an onboard computing device for triggering tactile alerts according to a schedule, a user interface device for acknowledging receipt of the tactile alert, and optionally, a fixture device for supporting an electrical device housing within a garment and/or a wireless connectivity device for receiving alert schedules and transmitting alert acknowledgements in conjunction with a hub.

In some embodiments, the fixture device is embodied by at least one permanent attachment device including, but not limited to, a chemical adhesive or stitched thread. In other embodiments, the fixture device is embodied by at least one removable attachment device including, but not limited to, a snap, zipper, hook-and-loop fastener, button, clip, or pin. In some embodiments, the fixture device is embodied by an accessible compartment within the garment especially suited to support the electrical device housing.

In some embodiments, the electromechanical transduction device includes a conductive wire coil and a magnetic structure free to move within the conductive wire coil. In some embodiments, the electromechanical transduction device comprises a conductive wire coil and a magnetic structure elastically suspended within the conductive wire coil.

In some embodiments, the electrical storage device is embodied by a battery or supercapacitor.

In some embodiments, the tactile alert device is replaced by a controller which feeds energy from the storage device into the coil winding to induce vibration of the encircled magnetic core.

In some embodiments, the garment is suited to cover the upper body. In some embodiments, the garment is suited to cover the lower body.

In some embodiments, the garment is an article of upper-body rehabilitation clothing including a collar, at least one sleeve, a torso portion with a front, a back, and two sides. The superior end of the torso portion is proximal to the collar and one or more sleeves, and a hem is at the inferior edge of the torso portion. The garment also may include at least one anterior torso access extending along the front of the torso portion from the collar to the hem, at least one arm access extending from the collar to the edge of the sleeve opening distal to the collar, and at least one side torso access extending along the side of the torso portion from the hem to a region of the torso portion superior to the hem. The accesses provide access to the body of a person wearing the article of clothing. The accesses may be constructed and arranged for providing said access without removal of the article of clothing from the body of said person wearing the article of clothing. Each access may be opened or closed by an incremental fastening device.

In some embodiments, the garment is an article of lower-body rehabilitation clothing including a waistline and at least one leg portion. The superior end of the leg portion is proximal to the waistline, and a hem is at the inferior edge of the leg portion. The garment may also include at least one knee access extending radially about the leg portion. The knee access allows an inferior portion to be detached from the article of clothing. The garment may also include at least one hip access extending from the waistline to a region of the leg portion inferior to the waistline.

The accesses may be constructed and arranged for providing said access without removal of the article of clothing from the body of said person wearing the article of clothing. Each access may be opened or closed by an incremental fastening device.

Other features and aspects of the present disclosure are discussed in greater detail below.

BRIEF DESCRIPTION OF THE DRAWINGS

A full and enabling disclosure of the present disclosure is set forth more particularly in the remainder of the specification, including reference to the accompanying figures, in which.

Figure 1:
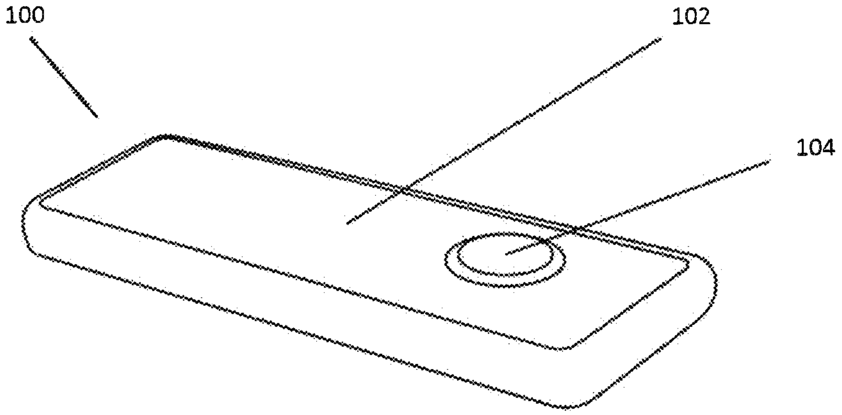
FIG. 1 depicts the form of a reminder device in one embodiment.

Repeat use of reference characters in the present specification and drawings is intended to represent the same or analogous features or elements of the present invention.

DETAILED DESCRIPTION

It is to be understood by one of ordinary skill in the art that the present discussion is a description of illustrative embodiments only and is not intended as limiting the broader aspects of the present disclosure.

In general, the device described in the present disclosure can be understood with respect to two main subsystems: a patient reminder system and a garment including a system of accesses which facilitate partial and complete dressing and undressing. The following discourse is organized according to the individual subsystems. The system of the present disclosure is particularly well suited to use with the clothing configurations disclosed in U.S. patent application Ser. No. 14/333,250 filed on Jul. 16, 2014 and which is herein incorporated by reference.

The patient reminder subsystem as incorporated into the disclosed rehabilitation garment may take many forms. In some embodiments, the system can be broken into two sub-subsystems: a medication reminder device, which may be embedded in a garment, and a hub, which is not necessarily near the patient.

In one embodiment, the medication reminder device comprises a housing, an electromechanical transduction device, an electrical energy storage device, an electrical coupling between the transduction device and the storage device, a tactile alert device, a user interface device, an onboard computing device, and optionally, a fixture device and/or a wireless communication device.

Figure 2:
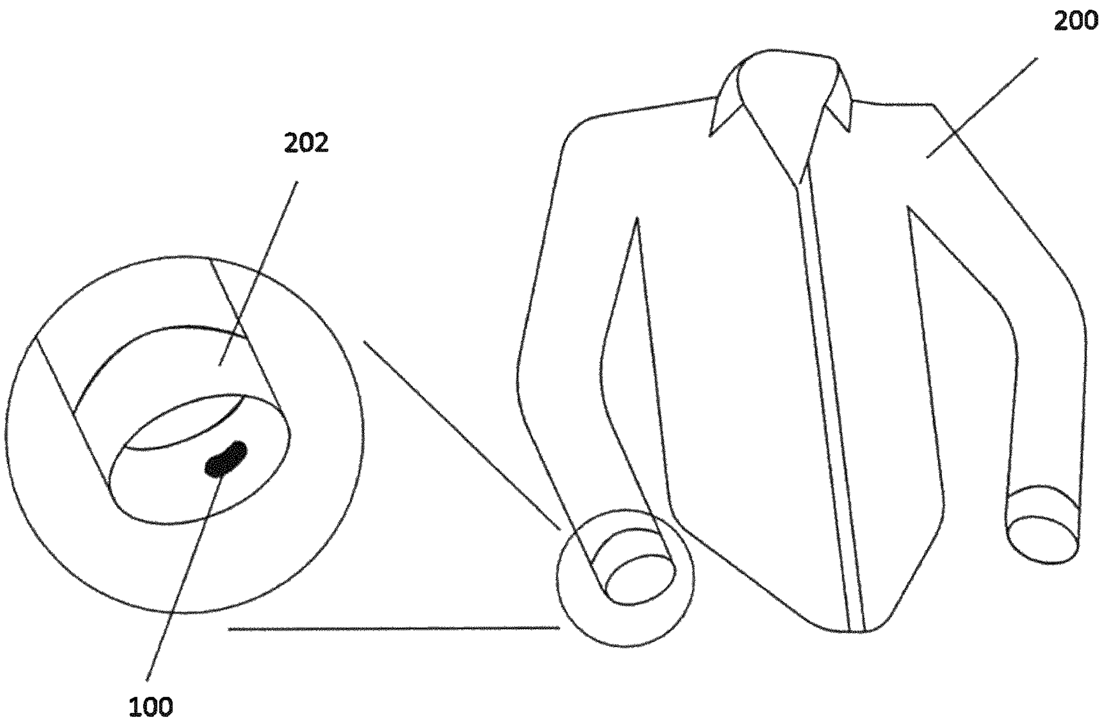
FIG. 2 depicts the location of a reminder device in cuff of upper body garment in one embodiment.
Figure 3:
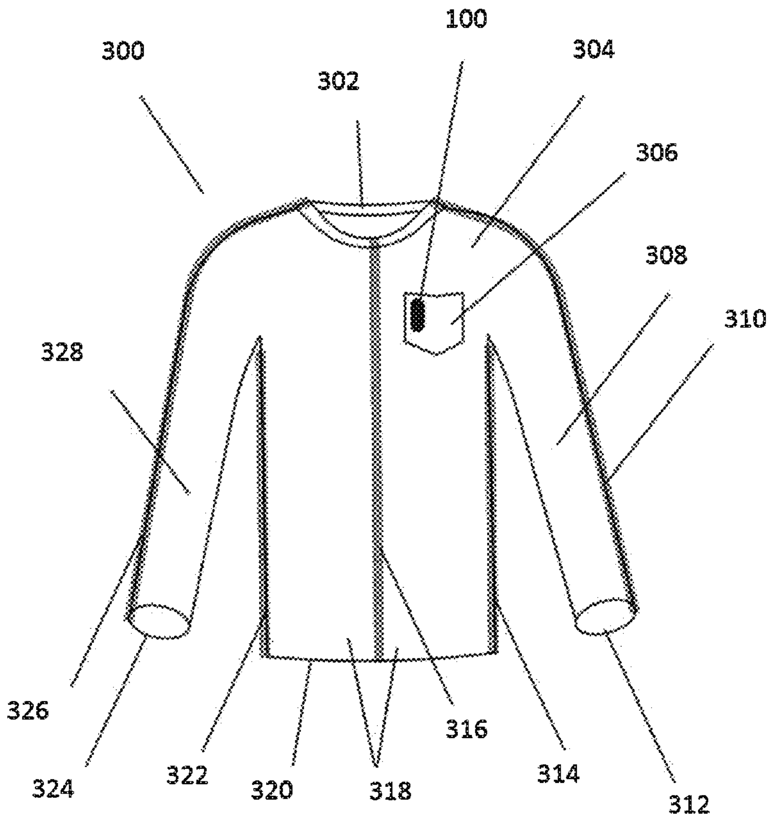
FIG. 3 depicts an upper body rehabilitation garment as configured in one embodiment.
Figure 4:
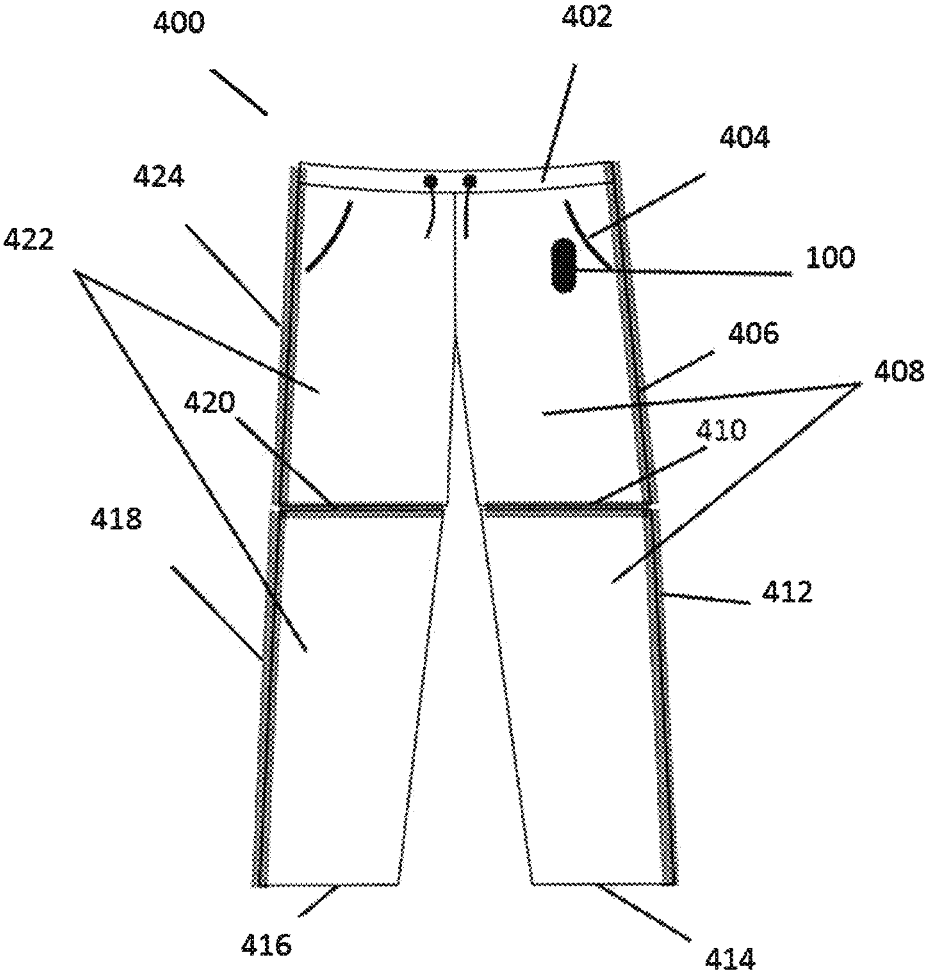
FIG. 4 depicts a lower body rehabilitation garment as configured in one embodiment.
Figure 7:
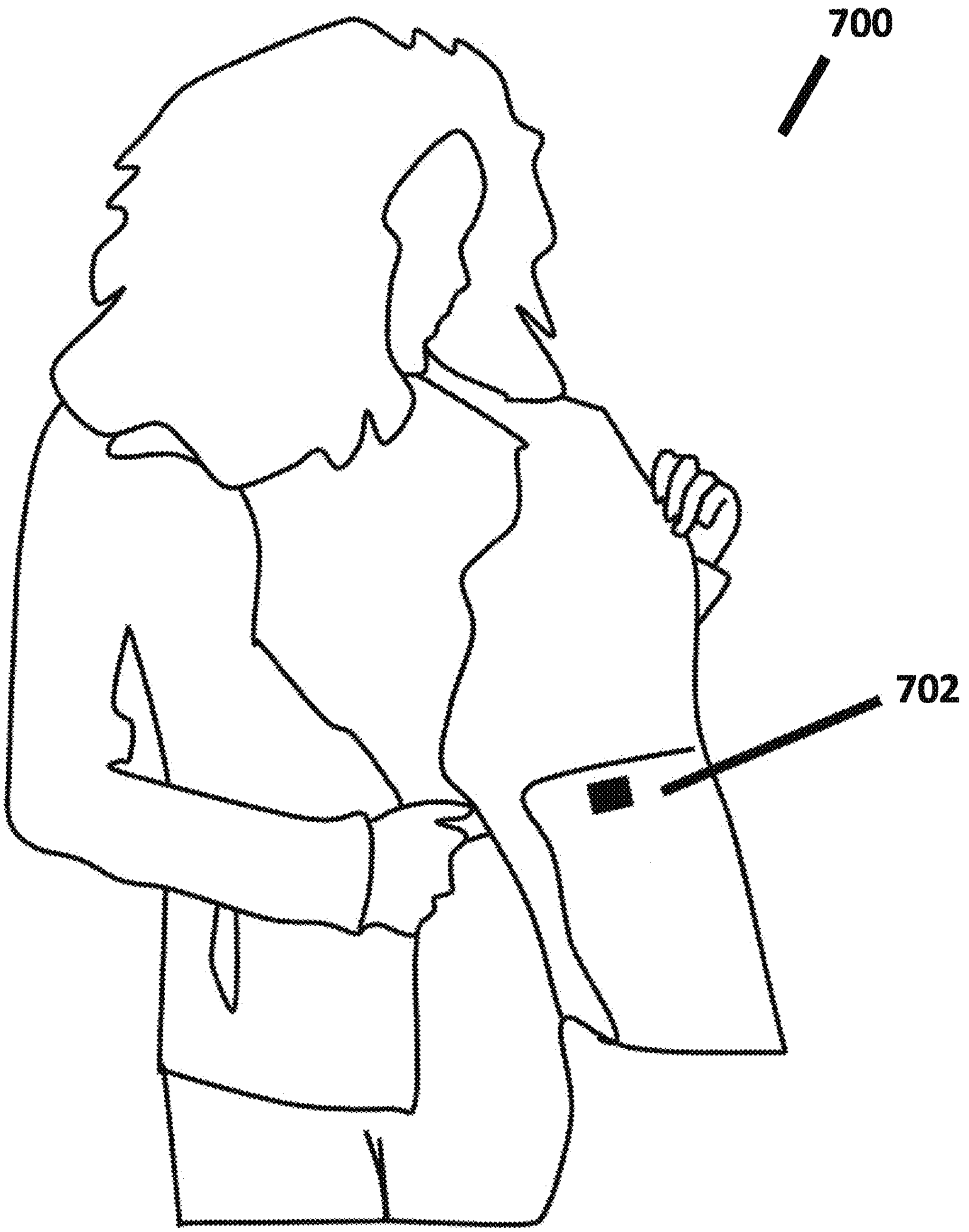
FIG. 7 depicts the location of a reminder device in one embodiment.

The fixture device secures the medication reminder device onto or within the garment. The medication reminder device can be situated in any convenient location within the garment. One example is shown in FIG. 2: the medication reminder device 100 might be situated in the cuff 202 of one sleeve of a shirt 200, to permit easy access with the opposing arm. Another example is shown in FIG. 3: the medication reminder device 100 might be situated in a breast pocket 306 of a shirt 300, facilitating easy use for wearers with limited mobility in one arm. Another example is shown in FIG. 7: the medication reminder device 702 is shown as placed in the pocket lining of a jacket 700 worn by a user. An example in a lower body garment 400 is shown in FIG. 4: the medication reminder device 100 might be situated in the lining of a front pocket 404, or along the waistline 402 (placement along waistline not shown). Although various embodiments of a medication reminder device comprising a fixture device are pictured, it is to be understood that the medication reminder device can also be substantially untethered and be used in a variety of positions not fixed within a garment.

The fixture device may secure the medication reminder device to the garment using a variety of attachment mechanisms. For example, a chemical adhesive could be used to bond the medication reminder device to the garment; thread could be used to mechanically restrain the medication reminder device within the garment; a compartment within the garment could be designed to tightly secure the medication reminder device; a separate base could be affixed to the garment such that the medication reminder device snaps in and out in a secure manner.

The medication reminder device housing 102 contains the components of the medication reminder device, with the possible exception of the transduction device. The housing may be waterproof to protect the internals of the medication reminder device when the garment is washed. The housing may also adopt any geometry depending on the ergonomic concerns introduced by placement within or on the garment. For example, if the medication reminder device is placed within a shirt or pants pocket, the medication reminder device housing may be slender in profile with flat faces conforming to the body of the wearer; the medication reminder device might be constructed from flexible materials to further improve the comfort of the wearer.

The electromechanical transduction device generates electricity when the garment is subjected to vibration, folding, shaking, or rubbing. The kinetic stimulus to the transduction mechanism might come from the motion of the wearer. If laundered in typical washing or drying machines, the garment will also experience vigorous agitation due to the tumbling or stirring motions of the laundry machine. If the transduction mechanism is optimized to harvest energy during a typical laundry cycle, the medication reminder device will provide a scalable alternative to traditional wearable technology that depends on manual battery charging or replacement. Typical wearable technology that depends on manual battery charging or replacement is not desirable in a medical facility or other environment that supports a large number of patients. A medication reminder device that recharges in the laundry requires no change to pre-existing garment handling and maintenance protocols, increasing the scalability advantage of the patient reminder subsystem over the current state of the art.

Figure 5:
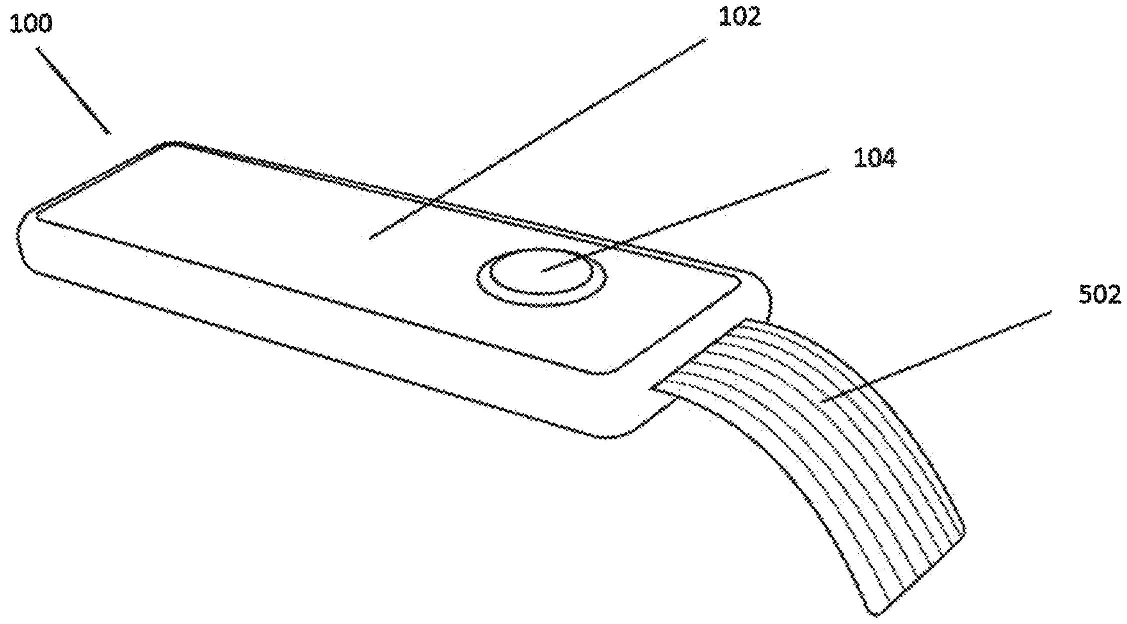
FIG. 5 depicts the form of a reminder device in one embodiment.

In one embodiment, the transduction mechanism may be a piezoelectric element. A piezoelectric element may be employed in a plurality of modes. For example, the internal circuits of the medication reminder device may be constructed on a flexible printed circuit board, and this board may be bonded to the piezoelectric element; when housed in a flexible housing, any deformation of the entire medication reminder device will produce a voltage across the terminals of the piezoelectric element. For a second example, one or more piezoelectric elements may be extended outside of the medication reminder device housing; as the garment deforms around the housing during vigorous agitation, the piezoelectric element 502 in FIG. 5 will produce a voltage across its terminals.

In one embodiment, a piezoelectric member may be configured to generate electricity optimally when exposed to the vigorous agitation of a laundry cycle. For example, the stiffness of the element must be compared with the stiffness of the fabric employed in the design. Additionally, the capacitance of the element must be selected for peak efficiency when the element is excited at frequencies near the typical tumbling frequency of garments in a washing or drying machine. The current state of the art aims to harvest maximum energy from body motion; body motion typically occurs at much lower frequencies than those experienced by a garment in a washing machine, so the design considerations in the state of the art would render inferior performance than that achieved by following the design considerations disclosed herein.

Figure 6:
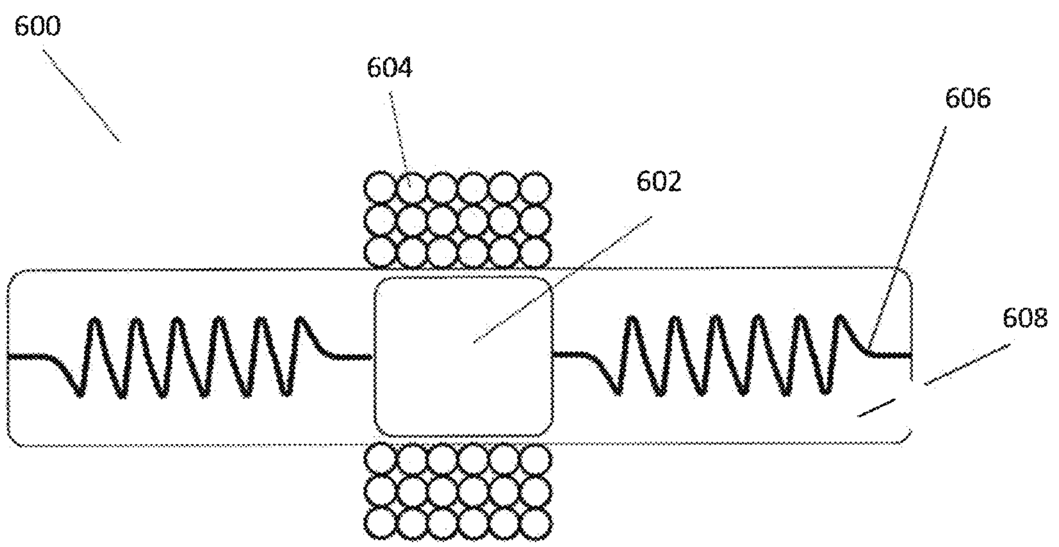
FIG. 6 depicts the form of a transduction device in one embodiment.

In one embodiment, the transduction mechanism may be an inductive generator 600 as shown in FIG. 6, comprising a magnet 602 enclosed in a tube with end caps 608, the tube being surrounded by a conductive coil of wire 604. The ends of the wire operate as the output terminals of the generator. The magnet may be formed from any permanently magnetic material; for example, a neodymium may be used. Furthermore, the magnet may be loosely contained within the tube to permit free oscillation. To minimize friction losses against the sides of the tube and provide for a tunable natural frequency, the magnet may be suspended from the end caps of the tube using elastic elements such as coil springs 606 or stretchable strings.

In one embodiment, the inductive generator may be configured to generate electricity optimally when exposed to the vigorous agitation of a laundry cycle. For example, the mass of the magnet and the stiffness of any elastic elements used can be manipulated to tune the natural frequency of the suspended magnet to exploit resonance near the typical tumbling frequency of garments in a washing or drying machine. Although some generators aim to harvest maximum energy from body motion, body motion typically occurs at much lower frequencies than those experienced by a garment in a washing machine. It is contemplated that some embodiments may employ wide-band generators which efficiently collect energy at a variety of frequencies, which may include both body motion frequencies and laundry cycle frequencies.

The electrical energy storage device collects the energy output by the transduction mechanism and supplies the necessary electricity to run the medication reminder device. The storage device can also be understood as a buffer which provides steady power output even when the medication reminder device is exposed to intermittent kinetic stimulus. The storage device may take many forms. In one embodiment, the storage device may be a rechargeable battery permanently or semi-permanently affixed within the internal circuitry of the medication reminder device. In one embodiment, the storage device may be a user-serviceable rechargeable battery that permits replacement once the battery has exhausted its charge-recharge cycles. In one embodiment, the storage device may be a supercapacitor permanently affixed within the internal circuitry of the medication reminder device.

The electrical coupling device provides an active electrical connection between the transduction mechanism and the electrical storage device. Furthermore, the coupling device must condition the electrical current or voltage emitted by the transduction element into a form usable by the electrical energy storage component. In one embodiment, the coupling may consist of a power conditioning circuit augmented with a charge status indicator; the charge status indicator may pass a signal to the onboard computing device to indicate a low charge.

The tactile alert device provides the user of the reminder device with vibratory notifications. The vibration source for the notifications can take many forms. If piezoelectric elements are used for transduction, the vibration may be produced by a dedicated motor with an eccentric mass on the tip. In another embodiment, wherein an inductive generator as described above is used, power from the storage device can be fed into the coil winding to induce motion of the encircled magnetic core. If the magnetic core within the generator is elastically suspended, the algorithm controlling the current to the coil winding can be optimized to exploit resonance of the vibrating magnet to produce strong vibration with very little energy expenditure.

The user interface device allows the user to control and respond to the reminder device. The user interface may adopt many forms. However, a simple user interface may include a single button 104. This button may be connected to a momentary type electrical switch. The user interface may also employ a microphone for voice-activated commands. Another embodiment may also include a speaker to relay audio alerts.

The user interface device is additionally customizable to suit the preferences of the user regarding interactions with the reminder device. In some embodiments, the user can, for example, adjust the volume level of the speaker in which audio alerts are relayed. The user interface device can further allow the user to set a specific time schedule in which various types of alerts are used. For example, the user can set the notification schedule to not allow audio alerts past a certain time and instead to use a vibrational reminder. The user interface device can allow the user to assign explicit alerts to differing events, e.g. a quick chime correlating with a predefined time of day to consume a medication, a long buzz indicating that the battery is low, or any combination of alerts with a user defined event. Furthermore, the user can customize the tone or pitch of the audible alert.

The user interface device can further be modified to suit the type of garment in which it is attached. Such a modification can include adjusting the intensity of the vibrational reminder based on the layering of the fabric it is encapsulated within. Further embodiments can include adjusting audio alerts based on the position of the device relative to the user.

The onboard computing device is responsible for managing the interactions of the medication reminder device components and executing standard medication reminder device software operations. The onboard computing device may be programmed to interpret a variety of inputs from the user interface device, including, but not limited to, a short button press, a long button press, or any predetermined sequence of short and long presses. The onboard computing device may have memory capability to permit the storage of medication schedules and may have the timing capability to execute actions according to said schedules. The onboard memory capability may also be employed to track a history of user inputs to monitor user adherence to the schedule.

The onboard computing device can additionally be customizable to suit specific characteristics of the user. In some embodiments, the onboard computing device can employ speech recognition capabilities, allowing the user interface to recognize the specific voice of the user in dictating certain commands.

The onboard computing device may also possess a self-diagnostic function to determine if any components of the medication reminder device are inoperable or need attention. For instance, the onboard computing device may monitor a low-charge indicator signal from the energy storage device and may alert the user to a state of low charge. In another embodiment, the diagnostic function may alert the user to any errors in the scheduling data.

The onboard computing device may further comprise a low medication function in which the user can predefine a notification to be triggered once a specified amount of medication is left on the current routine. In some embodiments, the user can customize the notification to be triggered once there are limited days left before a medication needs to be refilled.

The onboard computing device may have a reminder delay mode; in a situation where a patient is not near the needed medication, the patient may want to delay the reminder by any predetermined number of minutes so that the patient may be reminded again when the medication is accessible.

The onboard computing device may also have a panic mode which emits a distress signal after a predetermined user input. This distress signal may be audibly emitted by the reminder device or it may be transmitted wirelessly to the hub.

The wireless communication device supports communication between the medication reminder device and the hub. The wireless communication device may communicate directly with the hub, directly to the Internet, or both. The communication device may employ one or more standard protocols, including, but not limited to, Bluetooth, WiFi (e.g., according to IEEE 802.11), cellular signals, or near field communication protocols.

The hub is a central computing resource which may support the operation of one or more medication reminder devices. Examples of hub devices may include, but are not limited to, mobile devices (e.g., phones, tablets, laptops), stationary devices (e.g., personal desktop computers, servers), programmable microcontroller platforms, and smart devices (e.g., internet-connected televisions and appliances).

The hub may support functions used to view diagnostic data received from the reminder device, such as battery level, component malfunction, or corrupted schedule data. The hub may also be able to view the recorded history of user responses to scheduled reminders. The hub may also provide an interface to place reminder events on a schedule for the user and transmit the schedule to the reminder device. The hub may also provide a channel to contact a support team or archive of support documents to aid in troubleshooting or repairing the reminder device or garment or assist in the operation thereof.

The hub may also be capable of displaying an interface customized to the user based on certain medication routines, use of multiple reminder devices, or any combination of functions of the device that are incorporated here within. The user may further be able to control the specific features displayed within the interface based on personal preference.

In some embodiments, the diagnostic data received from the reminder device includes a time history of the charge in the electrical energy storage device. For example, this time history may be correlated to the activity of the wearer, allowing remote confirmation of the patient's activity. In some embodiments, the confirmation may indicate a completed schedule item. In some embodiments, the confirmation may be used as an emergency alert if no activity is detected after a predetermined amount of time.

In one embodiment, the functions of the hub may be supported by a Web interface. Authorized users may access the Web interface to remotely execute normal hub functions.

In one embodiment, the hub may allow the user to receive additional notifications through the form of a text message, phone call, app notifications on a mobile device, email, or any other suitable means. Such an embodiment can be optionally employed by the user if the wearable device fails, runs out of battery, or detects no motion for an extended period of time, such as in the case if the user is not wearing the device.

Garments configured with a system of accesses according to the present disclosure maintain both the comfort and dignity of the wearer by enabling selective access to a number of body parts or regions. The innovative features discussed herein provide no mandate on the style or overall appearance of the garment presently disclosed; the garment disclosed herein could be fashioned to suit the tastes and individual needs of any particular patient or healthcare provider. Any particular article or style of clothing mentioned in the present discussion is merely used for illustrative purposes.

The material selected to construct the garments disclosed herein may be chosen to meet the needs of a particular use case. For example, an antimicrobial fabric may be selected for use in a hospital environment, a heavy fabric may be selected to outfit patients who wish to garden outdoors, a soft fabric may be selected for patients needing rehabilitative sleepwear, or a breathable fabric may be adopted to produce rehabilitative active wear. As demonstrated, the present disclosure can be embodied by any number of materials.

The tailoring of any particular garment can be adapted for any range of body types or style preferences. Close-fitting garments and loose-fitting garments alike can be configured according to the present disclosure. The present innovation is not dependent on any particular style of clothing.

An upper-body garment configured according to the present disclosure may adopt many forms. Typically, however, the article will comprise: a collar which partially or completely encircles the neck of the wearer; at least one sleeve which covers some portion of the wearer's arm; and a torso portion which comprises a front panel, a back panel, and two side panels. The inferior edge of the torso portion can comprise at least one hem. The distal end of the sleeve may comprise a cuff. The following components described herein are shown in an illustrative example in FIG. 3: the garment 300, the collar 302, a left sleeve 308, a right sleeve 328, the front panel 318, a left cuff 312, a right cuff 324, and a hem 320.

The collar of the upper body garment can adopt many forms. The collar can be as simple as an elastic band, as in the style of a crew neck. Alternatively, an embodiment might employ a folding fabric collar, as in the style of an oxford shirt. If the garment takes the form of a jacket, a small vertical collar may be used, or a hood may be directly attached to the collar. The collar construction can mimic any number of conventional clothing styles, or any style required for a particular use.

The sleeve or sleeves of the upper body garment need not take any particular form. Patients without whole arms may be outfitted with only the number of sleeves they require. Sleeve design may be asymmetric to accommodate patients with asymmetric injuries or disabilities. When a sleeve is required to cover a patient's arm, it may extend as long or as short as desired. The embodiment may employ a cap sleeve, a full-length sleeve, or a sleeve of some intermediate length.

Any sleeve may include an arm access extending along some portion of the sleeve length. The origin and termination of the access may vary to accommodate the exposure needs of a patient. An incremental fastening device may be used to open and close the access when needed. For example, the access may be secured using hook-and-loop fasteners or a zipper. In the illustrative example in FIG. 3, both the left arm access 310 and the right arm access 326 extend from the collar 302 to their respective cuffs.

In one embodiment, a zipper may be used to secure the arm access. The zipper may be configured to permit different modes of body exposure. For example, a one way, closed zipper might extend from some point on or near the collar to some point on or near the cuff of the sleeve; if the closed end of the zipper is located nearest to the cuff, unzipping the zipper may provide access to the wearer's neck and shoulder; if the closed end of the zipper is located nearest the collar, unzipping the zipper provides access to the wearer's wrist, forearm, elbow, upper arm, and/or shoulder area. In another embodiment, a two way, closed zipper with closed ends on or near the collar and on or near the cuff may allow access to any region of the wearer's arm without undue exposure outside the area of interest.

The torso portion of the upper-body garment may include a front panel, back panel, and two side panels. These individual panels may incorporate accesses configurable to the wearer's needs. For example, the torso portion may incorporate at least one of the following elements: a front access, a side access, or a back access.

In one embodiment, shown in FIG. 3, a front torso access 316 may extend from the collar 302 to the hem 320 of the garment, aiding ingress into the garment and allowing access to the anterior torso region without removal of the garment. An incremental fastening device may be used to open and close the access when needed. For example, the access may be secured using hook-and-loop fasteners or a zipper. In one embodiment, a zipper may be used to secure the front torso access. The zipper may be configured to permit different modes of body exposure. For example, a one way, separating zipper might extend from the hem to the collar of the upper body garment, allowing easy ingress for the wearer and exposing the neck, chest, and abdominal regions; a two way, separating zipper might extend from the hem to the collar, allowing exposure of any region of the torso without undue exposure outside the area of interest.

In one embodiment, a side torso access may extend from some position on or superior to the hem to another position on or inferior to the sleeve, permitting access to the side of the wearer's torso without the removal of the garment. An incremental fastening device may be used to open and close the access when needed. For example, the access may be secured using hook-and-loop fasteners or a zipper. In one embodiment, a zipper may be used to secure the side torso access. The zipper may be configured to permit different modes of body exposure. For example, a one way, closed zipper might extend from some position on the hem to another position on or inferior to the sleeve; if the closed end is positioned nearest to the sleeve, unzipping the zipper permits access to the side of the wearer and loosens the fit of the hem around the wearer's body. In another embodiment, a two way zipper might extend from some position on or superior to the hem to another position on or inferior to the sleeve, allowing exposure of any region of the side of the torso without undue exposure outside the area of interest.

In the illustrative example shown in FIG. 3, the left torso access 314 and the right torso access 322 both extend from a point on the inferior edge of the sleeve opening proximal to the torso to a point on the hem 320.

In one embodiment, a back torso access may extend from some position on or near the collar of the upper body garment to some position on or near the hem, permitting inspection of the wearer's spinal region or any other area of interest of the posterior torso region. An incremental fastening device may be used to open and close the access when needed. For example, the access may be secured using hook-and-loop fasteners or a zipper. In one embodiment, a zipper may be used to secure the back torso access. The zipper may be configured to permit different modes of body exposure. For example, a two way, closed zipper might extend from some position on or near the collar of the upper body garment to some position on or near the hem, allowing exposure of any region of the back of the torso without undue exposure outside the area of interest.

A lower body garment configured according to the present disclosure may take many forms. Typically, the lower body garment may comprise a waistline and zero, one, or two leg portions. The inferior edge of a leg portion may comprise a hem. The following components described herein are shown in an illustrative example in FIG. 4: the garment 400, the waistline 402, a left leg assembly 408 with a left hem 414, and a right leg assembly 422 with a right hem 416.

The waistline of the garment may be constructed in any manner suiting the desired use case of the garment. For example, a cinch waistline or an elastic waistline may be employed for use in athletic or active wear, or a belted waistline may be employed for patients wishing to maintain a professional appearance throughout recovery. The waistline of the garment disclosed herein may mimic any number of conventional clothing styles, or any style required for a particular use.

In one embodiment, a lower body garment might be outfitted with a fly, mimicking conventional pants designs. In such a case, the fly may adopt any form of closure. For example, the fly may be secured by a zipper, by buttons, or by hook-and-loop fasteners.

The leg or legs of the lower body garment need not take any particular form. Patients without whole legs may be outfitted with only the number of legs they require. Leg portion design may be asymmetric to accommodate patients with asymmetric injuries or disabilities. When a leg portion is required to cover a patient's leg, it may extend as long or as short as desired. The embodiment may employ no leg portion, a short leg portion, a full-length leg portion, or a leg portion of some intermediate length. The legs may adopt features of conventional pants designs, such as hip pockets, back pockets, thigh pockets, or any such feature.

In one embodiment, a leg portion may be subdivided into an upper leg portion and a lower leg portion, with the upper leg portion remaining connected to the waistline and the lower leg portion remaining connected to the hem. In one embodiment, the placement of this separation may coincide with the general area of the wearer's knee. The inferior edge of the upper leg portion and the superior edge of the lower leg portion may be joined by some incremental fastening device positioned around the circumference of the leg portions. For example, the upper and lower leg portions may be mated by a zipper or a strip of hook-and-loop fasteners positioned around the coinciding edges of the leg portions. In the illustrative example shown in FIG. 4, the right leg is divided along the access 420 and the left leg is divided along the access 410.

In one embodiment, a side leg access may extend from some position on or superior to the hem of the leg portion to some position on or inferior to the waistline of the lower body garment, aiding ingress into the garment and facilitating localized exposure of regions along the side of the leg. An incremental fastening device may be used to open and close the access when needed. For example, the access may be secured using hook-and-loop fasteners or a zipper. In one embodiment, a zipper may be used to secure the side leg access. The zipper may be configured to permit different modes of body exposure. For example, a two way, closed zipper might extend from some position on or near the waistline of the lower body garment to some position on or superior to the hem, allowing exposure of any region of the hip, thigh, or side of the wearer's leg without undue exposure outside the area of interest.

In the illustrative example shown in FIG. 4, both the upper leg portion and the lower leg portion of each leg assembly is provided with a side access with an upper side leg access (left side—406, right side—424) and a lower side leg access (left side—412, right side—418).

These and other modifications and variations to the present invention may be practiced by those of ordinary skill in the art, without departing from the spirit and scope of the present invention, various embodiments of which are more particularly set forth in the appended claims. In addition, it should be understood that aspects of the various embodiments may be interchanged either in whole or in part. Furthermore, those of ordinary skill in the art will appreciate that the foregoing description is by way of example only, and is not intended to limit the invention so further described in such appended claims.

What is claimed:

1. A reminder device, comprising:

an electromechanical transduction device configured to generate electrical energy when agitated by a laundry machine during the course of a washing cycle or a drying cycle;

an electrical energy storage device;

an electrical coupling between the energy storage device and the electromechanical transduction device;

a tactile alert device;

an onboard computing device for triggering tactile alerts according to a schedule; and a user interface device for acknowledging receipt of the tactile alert.

2. The reminder device as defined in claim 1, further comprising a fixture device for supporting an electrical device housing within a garment.

3. The reminder device as defined in claim 2, wherein the fixture device comprises at least one permanent attachment device.

4. The reminder device as defined in claim 3, wherein the permanent attachment device includes at least one of a chemical adhesive and a stitched thread.

5. The reminder device as defined in claim 2, wherein the fixture device comprises at least one removable attachment device.

6. The reminder device as defined in claim 5, wherein the removable attachment device includes at least one of a snap, a zipper, a hook-and-loop fastener, a button, a clip, or a pin.

7. The reminder device as defined in claim 2, wherein the fixture device comprises an accessible compartment within the garment configured to support the electrical device housing.

8. The reminder device as defined in claim 1, wherein the electromechanical transduction device comprises a conductive wire coil and a magnetic structure free to move within the conductive wire coil.

9. The reminder device as defined in claim 1, wherein the electromechanical transduction device comprises a conductive wire coil and a magnetic structure elastically suspended within the conductive wire coil.

10. The reminder device as defined in claim 1, wherein the electrical storage device is embodied by a battery or supercapacitor.

11. The reminder device as defined in claim 8, wherein the tactile alert device is replaced by a controller which feeds energy from the storage device into the coil winding to induce vibration of the encircled magnetic core.

12. The reminder device as defined in claim 2, wherein the garment is configured to cover the upper body.

13. The reminder device as defined in claim 2, wherein the garment is configured to cover the lower body.

14. The reminder device as defined in claim 2, wherein the garment is an article of upper-body rehabilitation clothing comprising:

a collar;

at least one sleeve;

a torso portion comprising a front, a back, and two sides, wherein the superior end of the torso portion is proximal to the collar and one or more sleeves, and wherein a hem is at the inferior edge of the torso portion;

at least one anterior torso access extending along the front of the torso portion from the collar to the hem;

at least one arm access extending from the collar to the edge of the sleeve opening distal to the collar; and at least one side torso access extending along the side of the torso portion from the hem to a region of the torso portion superior to the hem;

wherein the accesses provide access to the body of a person wearing the article of clothing, the accesses being constructed and arranged for providing said access without removal of the article of clothing from the body of said person wearing the article of clothing, wherein each access is opened or closed by an incremental fastening device.

15. The reminder device as defined in claim 2, wherein the garment is an article of lower-body rehabilitation clothing comprising:

a waistline;

at least one leg portion, wherein the superior end of the leg portion is proximal to the waistline, and wherein a hem is at the inferior edge of the leg portion;

at least one knee access extending radially about the leg portion, wherein the knee access allows an inferior portion to be detached from the article of clothing; and at least one hip access extending from the waistline to a region of the leg portion inferior to the waistline;

wherein the accesses provide access to the body of a person wearing the article of clothing, the accesses being constructed and arranged for providing said access without removal of the article of clothing from the body of said person wearing the article of clothing, wherein each access is opened or closed by an incremental fastening device.

16. The reminder device as defined in claim 1, comprising a wireless connectivity device in communication with a hub to convey at least one of alert schedules, alert acknowledgements, and diagnostic data.

17. The reminder device as defined in claim 16, wherein the wireless connectivity device comprises at least one of a Bluetooth device, a cellular device, an wireless networking device, and a near-field communication device.

18. The reminder device as defined in claim 16, wherein the hub comprises at least one of a mobile device, a personal computer, and a server.

* * * * *